United States Patent
Szymaitis

(10) Patent No.: US 6,960,083 B2
(45) Date of Patent: Nov. 1, 2005

(54) DENTAL BUR

(76) Inventor: Dennis W. Szymaitis, 1172 Harvard Rd., Pittsburgh, PA (US) 15205

(*) Notice: Subject to any disclaimer, the term of this patent is extended or adjusted under 35 U.S.C. 154(b) by 211 days.

(21) Appl. No.: 10/403,605

(22) Filed: Mar. 31, 2003

(65) Prior Publication Data

US 2004/0191725 A1   Sep. 30, 2004

(51) Int. Cl.[7] .................................................. A61C 3/02
(52) U.S. Cl. ........................................ 433/165; 433/166
(58) Field of Search ............................... 433/165, 166; 408/199

(56) References Cited

U.S. PATENT DOCUMENTS

| | | | | |
|---|---|---|---|---|
| 4,834,655 A | * | 5/1989 | Kyotani | ............ 433/166 |
| 2002/0031745 A1 | * | 3/2002 | Kumar et al. | ............ 433/165 |

OTHER PUBLICATIONS

Brasseler USA catalog pp. 1.2-1.5, 1988.
"Evaluation of Surgical Debridement Bur for Use in Periodontal Surgery," by Cyril L. Evian, Robert A. Horowitz, E. Dwayne Karateew and David O. Maltz, *Compendium*, Nov. 1998.

* cited by examiner

*Primary Examiner*—Cary E. O'Connor
*Assistant Examiner*—Candice C. Stokes
(74) *Attorney, Agent, or Firm*—Buchanan Ingersoll PC

(57) ABSTRACT

A specialized dental bur designed to easily enter the periodontal pocket to perform root planing and curettage without the need for incisions has a cutting head attached to a shank. The cutting head has a combined structure of a narrow, hemispherical tip, cylindrical portion of larger diameter and a transition portion having a curved surface between them. Color coding or marking enables bur segregation and enables depth determination. The bur can be used for abrading tooth root, gingiva, and bone structures without gingival incisions.

18 Claims, 2 Drawing Sheets

DENTAL BUR

FIELD OF INVENTION

The invention relates to a rotary bur used to abrade the surface of the root and the adjacent gingival tissues for use with periodontal structure regeneration material, for root planing and gingival curettage, for treating periodontal disease.

BACKGROUND OF THE INVENTION

Periodontal disease occurs when bacteria colonize the sulcus space between the teeth and gingiva. The bacteria cause inflammation. The inflammation destroys the inner surface of the sulcus altering the structure from a normal epithelial cover to a surface devoid of epithelium. With the epithelial barrier destroyed, bacterial inflammation advances and destroys the periodontal attachment structures of connective tissue and bone, and stimulates a growth of granulation tissue on the inner damaged gingival surface. The inflammation then progresses down the root toward the apex of the root. As periodontal disease progresses, open pocket develop between the tooth and the gingiva. The root surface becomes contaminated with biofilm, bacterial toxins and hard adherent calcified calculus deposits.

A primary method to treat periodontal disease is to remove or debride granulation tissue and scrape the root surface clean. This procedure is done during non-surgical root planing and curettage, and surgical periodontal therapy. During root planing and curettage, operator access to the depth of the periodontal pocket is hindered since the instrument must be inserted into the limited space between the root and gingiva. In the hands of the most experienced operators, root planing and curettage cannot completely remove the hard deposits and biofilm even when utilizing both specialized hand and ultrasonic instruments as demonstrated in a recent study using fiberoptics (Perioscopy) to examine treated root surfaces. *A Clinician's 3 Year Experience With Perioscopy*, Dr. Roger Stambaugh, Compendium November 2002 Vol. 23, No 11A. Periodontal surgery allows a higher degree, but not complete cleaning, of root deposits. Periodontal surgery requires incisions to peel back the gingiva to allow the operator access to the root deposits.

Hand instruments are complex in design and require numerous compound shaft angles mated with a myriad of shaped scraping edges to allow the operator to clean complex curves of root surfaces in obscure positions in the mouth. have been designed number in the thousands. Ultrasonics utilize electronics to generate a vibrating insert tip to clean the root. Ultrasonic inserts are manufactured in approximately 30–50 different sizes, designs, and angles to allow placement of the ultrasonic cleaning tip along side the roots. Hand instruments cost on average from $7.00 to $27.00 with ultrasonic inserts averaging from $80.00 to $145.00.

There is one type of powered rotary bur, the Evian Debridement Bur, designed to remove granulation tissue and root deposits. This bur cleans the root after the gingiva is incised with scalpels, loosened, and peeled away from the bone and tooth. The Evian burs have round ends varying in diameter from 1.0 mm to 1.8 mm with non-cutting grooves. Evian burs are specifically designed not to abrade the root surface. The Evian bur generally has a diameter greater than the width of the space between the tooth and gingiva and cannot easily enter the narrow periodontal pocket between the tooth and gingiva without incisions to create a wider entry space; therefore its use is limited to surgical procedures.

The objective of root planing is to remove root deposits, granulation tissue, and to detoxify the root surface of imbedded bacterial toxins. The stated goal of hand instruments, ultrasonic instruments and the Evian Bur is to remove as little of the root surface as possible. Microscopic studies reveal that these instruments achieve their goal and only gently clean the root surface leaving small scratch marks. However, root surfaces are irregular and porous. Toxic bacterial byproducts penetrate the root surface or are concealed within the irregular root surface. A disadvantage with these existing instruments is that they are specifically designed to not abrade the outer irregular root surface, and therefore they do not detoxify the root surface.

What is needed is a rotary bur designed to function without surgery, designed to enter the pocket without trauma to the tissue at the entrance of the pocket, to detoxify the root by abrading the outer surface of the root, and to debride the granulation tissue lining the periodontal pocket. I call the process of simultaneously removing the granulation tissue, removing the root deposits, and sanding off the outer root surface without the need for incisions "bur abrasion". A further advantage is that dentin exposed by bur abrasion provides a natural source for bone morphogenic protein that speeds periodontal healing.

Some of the presently manufactured burs have a taper from a hemispherical tip to the base of the cutting head. This taper is a straight line and cannot conform to the compound curves of the root and therefore cannot adequately debride the gingiva or root.

Other common burs, such as the 1157R, are also not adequate to perform the required tasks of bur abrasion. The 1157R is a cylinder shape with its parallel sides capped by a hemisphere tip. The hemisphere tip diameter is equal to the width of the parallel sides. This blunt shape is too wide to easily enter the space between the gingiva and root without tearing the gingival tissue during placement into the periodontal pocket. To enter the periodontal pocket without trauma to the tissue requires a marked difference in design of the tip of the bur.

SUMMARY OF THE INVENTION

I provide a bur designed to perform the bur abrasion procedure without the need for incisions. During root planing and curettage and surgical procedures, the bur abrasion procedure simultaneously removes granulation tissue from the inner lining of the gingiva, biofilm and calculus from the roots, and abrades the root to detoxify the root of bacterial toxins. Bur abrasion exposes bone morphogenic protein to speed healing.

The bur has a unique end design to allow ease of insertion into the space between the gingiva and root. The end is hemispherical having a diameter less than the diameter of the parallel sides of the cutting head of the bur. A transition length of approximately 1 mm from the hemispherical tip to the wider cutting head preferably has an outer surface that forms an arc. This arc changes to match different diameters of cutting heads. The combined structure of a small hemispherical tip with the translation length function as a wedge to allow easy access into the periodontal pocket. The combined structure allows close contact with the compound curves of the root.

I further provide a method of using this bur to simultaneously abrade granulation tissue from the gingival pocket and abrade the outer surface of the root. I also use the bur to detoxify the root by removing the outer contaminated root layer. Bur abrasion removes all adherent biofilm. This method can be performed without surgical incisions.

The present bur is preferably used to do root planing and curettage in lieu of hand instruments and ultrasonics.

I further prefer to use the bur to expose bone morphogenic proteins present naturally in dentin. The abraded dentin is a source for natural bone morphogenic protein.

Other objects and advantages of the present invention will become apparent from the description of certain present preferred embodiments thereof which are shown in the drawings.

BRIEF DESCRIPTION OF THE PREFERRED EMBODIMENTS

Figure 1:
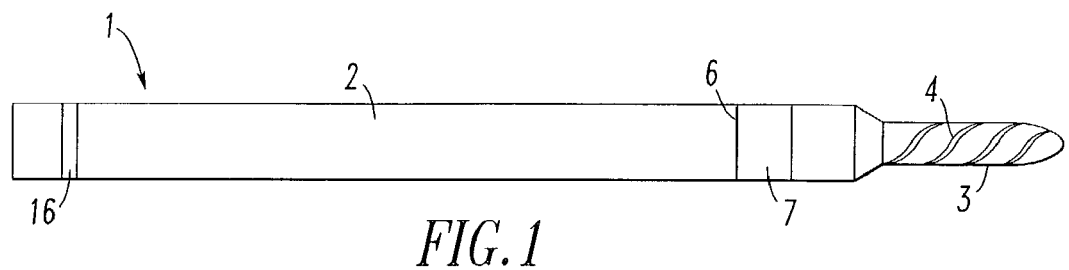
FIG. 1 is a side view of a first preferred embodiment of my dental bur.

A first present preferred embodiment of my dental bur 1 shown in FIG. 1 has a generally cylindrical shank 2 with a cutting head 3 having cross cut or straight cutting edges 4. This embodiment 7 has a series of concentric rings 6 or 7 that will indicate the depth in which the bur has been inserted into the periodontal pocket. The rings 6 or the regions 7 could be different colors. A band 16 can be provided around the shank which indicates the length of the bur, the length of the cutting head, the diameter of the cutting head, or perhaps all such dimensions.

The cutting head can be one of several lengths preferably ranging from 2 mm to 7 mm, although I prefer the standard 4.2 mm.

Figure 2:
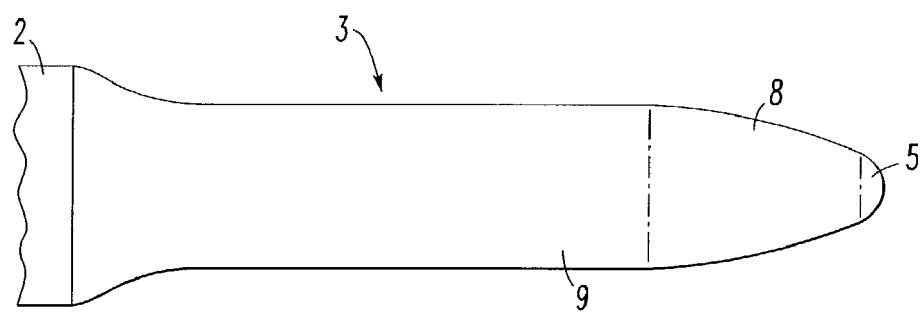
FIG. 2 is an enlarged profile of the cutting head in the dental bur of FIG. 1.
Figure 3:
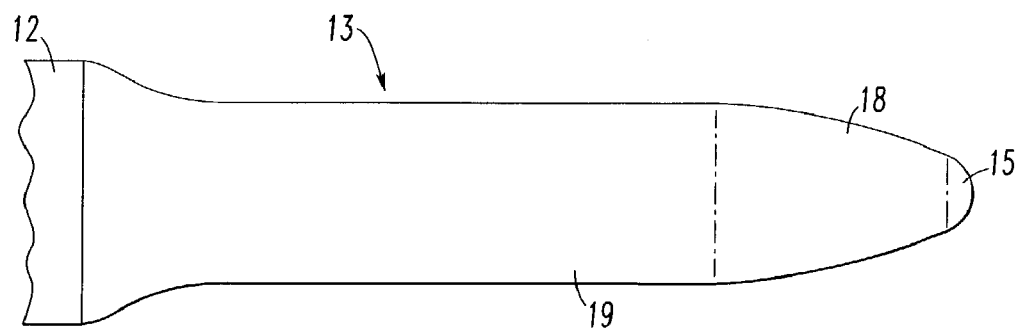
FIG. 3 is an enlarged profile similar to FIG. 2 of a second preferred the cutting head.

Two present preferred profiles of the cutting head are shown in FIGS. 2 and 3. Both embodiments have a hemispherical tip 5 and 15. A transition portion 8, 18 connects the tip 5, 15 to a cylindrical portion 9, 19 of the cutting head. The cylindrical portion 9, 19 is attached to the shank 2, 12. The dotted lines in FIGS. 2 and 3 are provided to enable the reader to readily distinguish the transition portion from the tip and from the cylindrical portion of the cutting head.

The tip 5, 15 is a hemisphere but of a smaller diameter than the diameter of the cylinder shaped portion 9, 19. The tip diameter can be 0.25 mm to 0.75 mm although I prefer 0.38 mm. The length of the transition position 8, 18 can be 0.25 mm to 2 mm although I prefer 1 mm. This transition position 8 has an outer surface that forms an arc from the tip 5 to the cylindrical portion 9. This arc is formed from a circle with the radius from 2 mm to 8 mm, although I prefer 4 mm. If desired, the transition could have a longer, more gentle arc-like transition portion 18. The combined structure of a smaller diameter hemispherical tip with the transition length functions as a wedge and allows entrance into the periodontal pocket without trauma by easily expanding the pocket to accept the remainder of the bur. A standard bur with a hemispherical rounded end is just too wide to easily enter the space between the tooth and the gum and can cause tears in the gum. The present bur overcomes this problem. An additional usefulness of the combined structure is that it generally conforms to the irregular compound curves found in root anatomy, and with manipulation, allows easy access to abrade both root and gingiva. The cutting edges of the bur can be either cross cut or straight. The burs may have cutting edges of the rose cut, group cut or other cut. The cutting edges extend over the smaller hemispherical tip. The cutting edges are designed to prevent clogging.

I prefer to construct the dental bur with the common shank sizes of 19 mm and 25 mm, although lengths of 15 mm to 30 mm are feasible. I also prefer to supply a size I call Mid-Shank at 22 mm. Two aspects of conducting bur abrasion are length of the shank required to penetrate to the depth of the periodontal pocket, and constraints of limited space in the oral cavity. Pocket depths too deep for the 19 mm shank require the use of the 25 mm shank. However the longer 25 mm shank presents difficulties with manipulation in many areas of the oral cavity due to limited access. I have found that the 22 mm shank effectively reaches the majority of pocket depths and overcomes the limited space problem. An additional advantage is that the multiple times the operator has to change from the 19 mm shank to the 25 mm shank decreases. The 22 mm provides a great advantage in time saving.

I also provide for both a depth marking and color-coding for the burs. Pockets are depth measured prior to surgery. Burs with depth indicators such as concentric rings at specified depths or different colors at specified depths accomplish the required depth feedback to the operator. The different shank lengths or head sizes can also be color coded or marked for easy identification.

The bur abrasion burs can have cutting heads in various diameters from 0.5 mm to 2 mm. I prefer sizes 0.9 mm, 1.0 mm, and 1.2 mm. The difference in head diameters is slight but crucial when attempting to penetrate a periodontal pocket on anterior teeth where the pocket width between the root and gingival tissue is narrower than the posterior teeth. Using a wider posterior bur such as a 1.2 mm diameter on anterior teeth with a much narrower periodontal pocket opening could result in gingival trauma. Color-coding eliminates this potential error.

Figure 4:
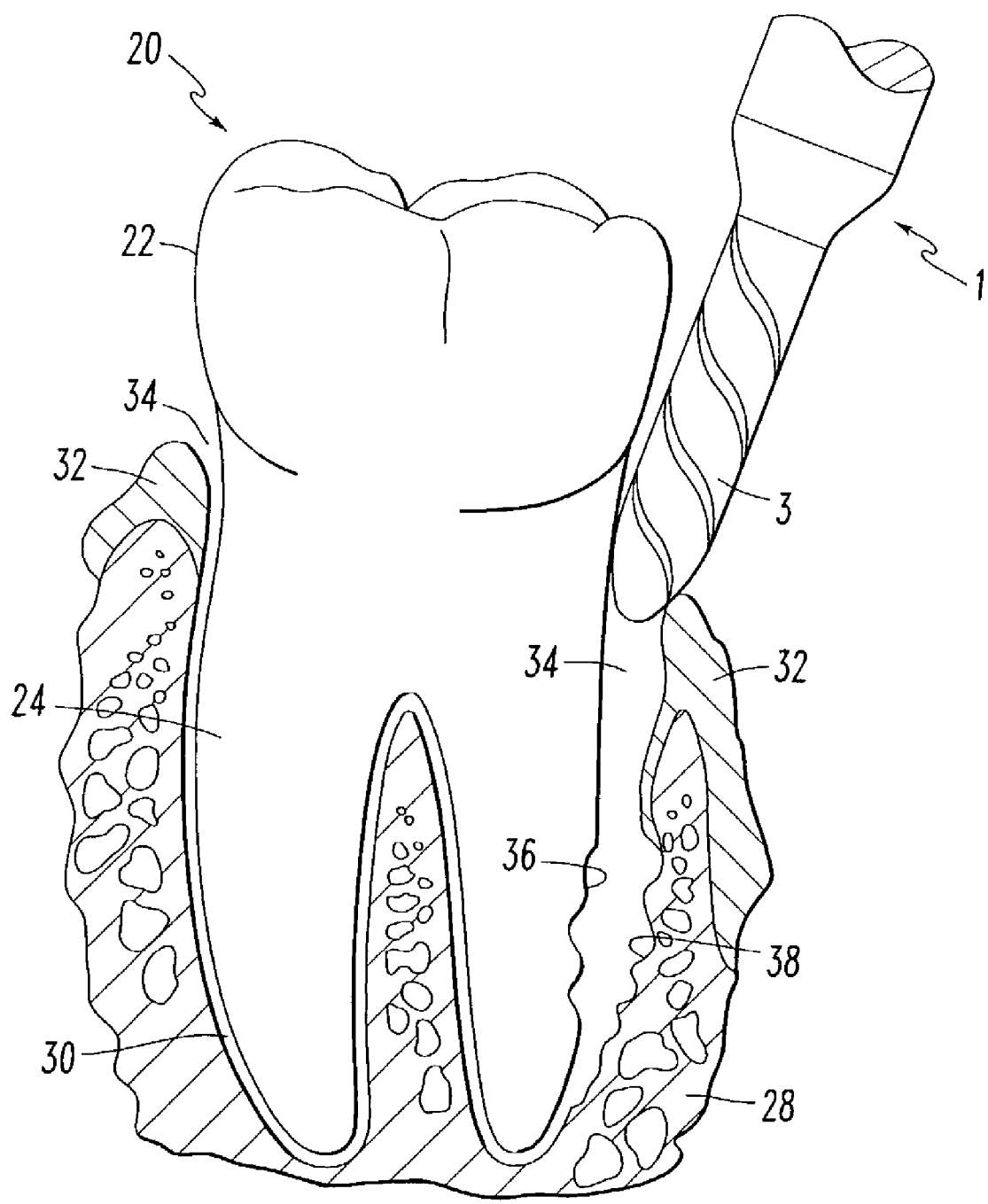
FIG. 4 is a side view of a damaged tooth illustrating insertion of the bur in accordance with the present preferred methods of using the bur.

Referring to FIG. 4, a tooth 20 has a crown 22 and root 24. Nerves and blood vessels pass from the base of the root 24 through a bone 28 that surrounds the root 24. There is a periodontal ligament 30 surrounding much of the root 24 and gum or gingiva 32 around the upper part of the root and the base of the crown 22. There is a pocket 34 between the gingiva 32 and the root 20. In a healthy tooth this pocket 34 is very shallow, typically one to three millimeters. Bacteria colonize the pocket. These bacteria cause the pocket 34 to deepen. As periodontal disease progresses, the bacteria cause inflammation that destroys the ligament and bone creating depressions 38 in the bone. The bacteria may even damage the root as indicated by the damaged area 36 in FIG. 4.

The conventional way of treating advanced periodontal disease is to create incisions to reflect the gingiva 32, remove the damaged bone with hand instruments or sand areas 36 and 38 with rotary burs, remove all debris from the sanding, place a bone growth material adjacent the sanded bone surfaces and suture the gingiva. Using the bur shown in FIGS. 1 through 3 I provide a method that does not involve incisions in the gingiva. I abrade the root surface and inner surface of the gingiva first with the dental bur 1, producing dentin particles and loose granulation tissue. I have found that the bone seems to grow better if I do not rinse the abraded particles out of the pocket. Tooth dentin is a natural source of bone morphogenic protein and I utilize this source to promote bone regeneration. This failure to rinse is contrary to present dental practice. Standard periodontal practice is to completely clean the pocket of all abraded bone and to remove all granulation tissue. To abrade the root and gingival surfaces I simply place the dental bur into the pocket, but do not incise the gums. The bur can be oriented from a vertical position to a near horizontal position as required to reach damaged areas.

After abrading, specially designed gauze is placed into the 1–1.5 mm created space to both distend the pocket and create hemostasis with or without chemicals. The gauze can carry and place antibacterial materials, antibiotics, bone growth substances, or any type of root conditioning materials. Sufficient time is allowed for hemostasis, distention, and the placed materials to function as designed, then the gauze is removed. At this stage, I use a syringe to inject periodontal structure regeneration composition, that is composed of finely ground bone growth material mixed with collagen particles, into the pocket.

The present bur can also be used in standard root planing and cutterage procedures. However, when using the present bur to abrade root surfaces, no surgical incisions are needed and they should not be made. Conventional root planing is difficult, boring and is only 90% to 95% effective in removing root contamination even in the best professional hands. Root planing using the bur here disclosed is easy, equally or more effective, and could be performed by most, if not all, dentists and dental hygenists.

An important advantage of the methods here described is that the methods can be performed without using hand instruments or ultrasonic devices. Indeed, the methods here described can be practiced by any dentist and do not require the skills or the facilities of a periodontist.

While I have shown and described certain present preferred embodiments of my dental bur, it should be understood that my invention is not limited thereto, but may be various embodied within the scope of the following claims.

I claim:

1. An improved dental bur of the type having a cylindrical shank of a selected diameter and a cutting head attached to the shank wherein the cutting head comprises:
    a cylindrical portion extending from the shank, and having a first diameter;
    a hemispherical tip at a distal end of the cutting head, the tip having a tip diameter of from 0.25 mm to 0.75 mm, the tip diameter being less than the first diameter; and
    a transition portion connecting the tip to the cylindrical portion, the transition portion having a diameter at an end attached to the cylindrical portion which is equal to the first diameter and having as second diameter at an opposite end which is equal to the tip diameter wherein a line along an outer surface of the transition portion from the cylindrical portion to the hemispherical tip forms an arc.

2. The improved dental bur of claim 1 wherein the arc is a segment of a circle having a radius of from 2 mm to 8 mm.

3. The improved dental bur of claim 2 wherein the radius is 4 mm.

4. The improved dental bur of claim 1 wherein the transition portion has a length of from 0.25 mm to 2 mm.

5. The improved dental bur of claim 4 wherein the length is 1 mm.

6. The improved dental bur of claim 1 wherein the shank has a length of from 15 mm to 30 mm.

7. The improved dental bur of claim 6 wherein the length is one of 19 mm, 22 mm and 25 mm.

8. The improved dental bur of claim 1 also comprising depth indicators on the cutting head or shank.

9. The improved dental bur of claim 8 wherein the depth indicators are concentric rings.

10. The improved dental bur of claim 8 wherein the depth indicators are regions of different colors on the cutting head or shank.

11. The improved dental bur of claim 1 also comprising at least one marking on the shank, the marking being an indicator of at least one of shank length and cutting head size.

12. The improved dental bur of claim 1 wherein the cutting head has a length of from 2 mm to 7 mm.

13. The improved dental bur of claim 1 wherein the cutting head has cutting edges which are cross cut or straight.

14. A method of abrading at least one of a root surface of a tooth and granulation tissue from a gingival pocket surrounding the tooth comprising:
    selecting a bur having a cylindrical shank of a selected diameter and a cutting head attached to the shank wherein the cutting head comprises:
        a cylindrical portion extending from the shank, and having a first diameter;
        a hemispherical tip at a distal end of the cutting head, the tip having a tip diameter of from 0.25 mm to 0.75 mm, the tip diameter being less than the first diameter; and
        a transition portion connecting the tip to the cylindrical portion, the transition portion having a diameter at an end attached to the cylindrical portion which is equal to the first diameter and having a second diameter at an opposite end which is equal to the tip diameter wherein a line along an outer surface of the transition portion from the cylindrical portion to the hemispherical tip forms an arc;
    inserting the bur into the gingival pocket surrounding the tooth; and
    abrading at least one of a root surface of a tooth and granulation tissue from the gingival pocket surrounding the tooth.

15. The method of claim 14 wherein an outer contaminated root layer is removed.

16. The method of claim 14 wherein the root surface is abraded and no surgical incisions are made to abrade the root surface.

17. A method of planing a root surface of a tooth comprising:
    selecting a bur having a cylindrical shank of a selected diameter and a cutting head attached to the shank wherein the cutting head comprises:
        a cylindrical portion extending from the shank, and having a first diameter;
        a hemispherical tip at a distal end of the cutting head, the tip having a tip diameter of from 0.25 mm to 0.75 mm, the tip diameter being less than the first diameter; and
        a transition portion connecting the tip to the cylindrical portion, the transition portion having a diameter at an end attached to the cylindrical portion which is equal to the first diameter and having as second diameter at an opposite end which is equal to the tip diameter wherein a line along an outer surface of the transition portion from the cylindrical portion to the hemispherical tip forms an arc;
    inserting a portion of the bur into the gingival pocket surrounding the tooth; and
    planing the root surface.

18. The method of claim 17 wherein the method is performed without using hand instruments or ultrasonic devices.

* * * * *